US012758178B2

(12) United States Patent
Dieck et al.

(10) Patent No.: US 12,758,178 B2
(45) Date of Patent: Oct. 13, 2026

(54) IMAGING SYSTEM PHANTOM

(71) Applicant: GE Precision Healthcare LLC, Waukesha, WI (US)

(72) Inventors: Mason Dieck, Milwaukee, WI (US); Sam Maule, Hartford, WI (US); Michelle Marie Severino DeLong Samalik, Waukesha, WI (US); Daisy Cueto, West Allis, WI (US); Chelsey Amanda Lewis, Waukesha, WI (US); John M. Boudry, Waukesha, WI (US); Arka Datta, Täby (SE)

(73) Assignee: GE PRECISION HEALTHCARE LLC, Waukesha, WI (US)

(*) Notice: Subject to any disclaimer, the term of this patent is extended or adjusted under 35 U.S.C. 154(b) by 152 days.

(21) Appl. No.: 18/732,455

(22) Filed: Jun. 3, 2024

(65) Prior Publication Data

US 2025/0366814 A1 Dec. 4, 2025

(51) Int. Cl.

| | |
|---|---|
| ***A61B 6/00*** | (2024.01) |
| ***A61B 6/03*** | (2006.01) |
| ***A61B 6/58*** | (2024.01) |
| *A61B 6/04* | (2006.01) |

(52) U.S. Cl.

CPC .............. *A61B 6/584* (2013.01); *A61B 6/035* (2013.01); *A61B 6/0487* (2020.08)

(58) Field of Classification Search

CPC ................................ A61B 6/583; A61B 6/584

See application file for complete search history.

(56) References Cited

U.S. PATENT DOCUMENTS

| | | | | |
|---|---|---|---|---|
| 2020/0368551 | A1* | 11/2020 | Bassalow | A61N 5/1049 |
| 2022/0313203 | A1 | 10/2022 | Zhan et al. | |
| 2022/0395248 | A1 | 12/2022 | Yokoi | |

FOREIGN PATENT DOCUMENTS

| | | | | |
|---|---|---|---|---|
| JP | 2017077271 A | 4/2017 | | |
| JP | 6562812 B2 * | 8/2019 | | A61B 6/582 |
| JP | 2020500062 A | 1/2020 | | |

OTHER PUBLICATIONS

JP6562812 (English translation) (Year: 2019).*

EP application 25175378.6 filed May 9, 2025—extended Search Report issued Oct. 21, 2025; 8 pages.

JP6562812—English Abstract not available; English Abstract of corresponding document JP2017077271A provided, Espacenet.com Jan. 16, 2026.

JP application 2025-080324 filed May 13, 2025—office action issued Apr. 2, 2026; Machine Translation, 7 pages.

JP2017-077271 English Abstract, Espacenet.com Jun. 23, 2026; 1 page.

JP2020-500062 English Abstract, Machine Translation, Espacenet.com Jun. 23, 2026; 3 pages.

* cited by examiner

*Primary Examiner* — Dani Fox

(74) *Attorney, Agent, or Firm* — McCoy Russell LLP

(57) ABSTRACT

Embodiments of a phantom for calibrating an imaging system are disclosed herein. In one example, a phantom for an imaging system includes a base comprised of a first material, a plurality of layers positioned on the base, each layer of the plurality of layers comprised of the first material or one or more additional materials, and a plug coupled to a front face of the base and the plurality of layers, the plug configured to couple to an accessory slot of a patient table of the imaging system.

20 Claims, 14 Drawing Sheets

IMAGING SYSTEM PHANTOM

TECHNICAL FIELD

Embodiments of the subject matter disclosed herein relate to a phantom, and more particularly, to a phantom used to calibrate a photon counting computed tomography (CT) scanner.

BACKGROUND

In computed tomography (CT) imaging systems, an electron beam generated by a cathode is directed towards a target within an X-ray source or X-ray tube. A fan-shaped or cone-shaped beam of X-rays produced by electrons colliding with the target is directed towards a subject, such as a patient. After being attenuated by the object, the X-rays impinge upon an array of X-ray detectors, generating an image. One example of a CT system is a Photon Counting CT (PCCT), where the X-ray detectors are photon-counting detectors, and photons are counted to provide spectral information. A calibration process may be performed periodically on the PCCT system to obtain projection data of materials that simulate varying human tissue densities. The calibration process may include performing a CT imaging procedure on an object, referred to as a phantom.

SUMMARY

In one example, a phantom for an imaging system includes a base comprised of a first material, a plurality of layers positioned on the base, each layer of the plurality of layers comprised of the first material or one or more additional materials, and a plug coupled to a front face of the base and the plurality of layers, the plug configured to couple to an accessory slot of a patient table of the imaging system.

The above advantages and other advantages and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
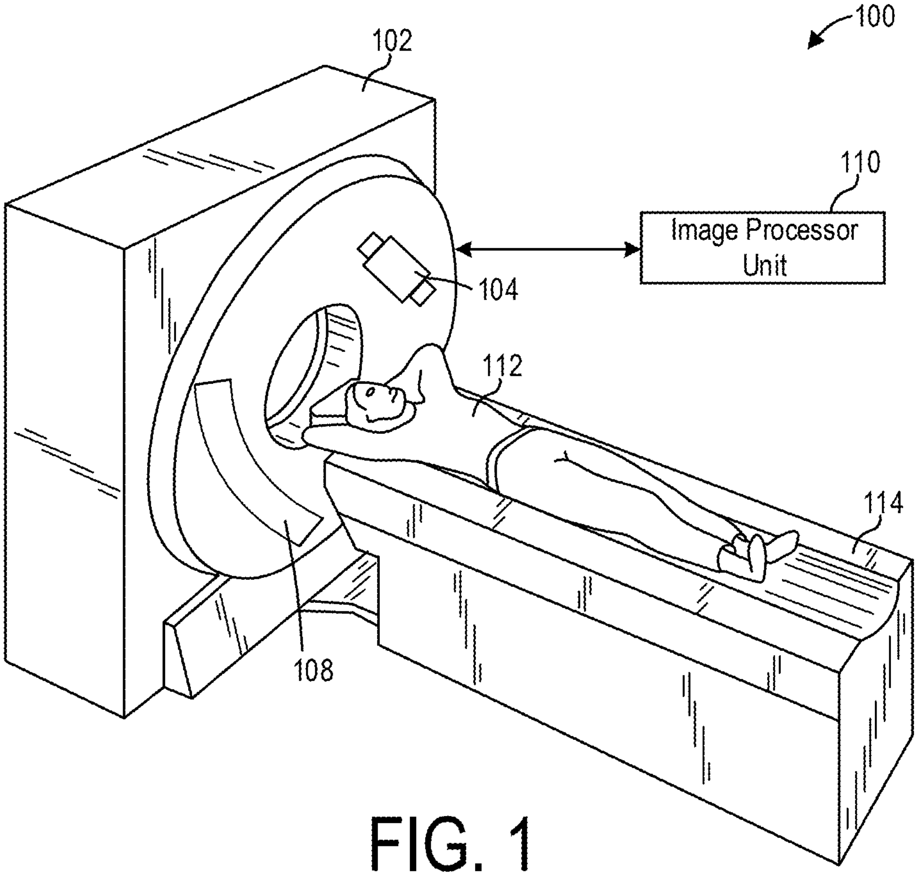
FIG. 1 shows a pictorial view of a computed tomography (CT) imaging system, in accordance with one or more embodiments of the present disclosure.

The description and embodiments of the subject matter disclosed herein relate to a phantom for calibration scans of an imaging system, such as a photon counting computed tomography (PCCT) system. Imaging systems, such as PCCT systems, may demand regular calibration scans, such as daily or weekly calibration scans to offset any gain drift, realized from hardware such as X-ray tube focal spot position change, or radiation degradation of the detectors. Further, PCCT systems may obtain spectral information that allows generation of basis material decomposition (BMD) images. Calibrating PCCT systems may thereby demand that calibration projection data be obtained that mimics the materials and material thicknesses of the human body. Thus, phantoms for calibrating PCCT systems may include multiple different materials, such as polyvinyl chloride (PVC) and polyethylene (PE). However, such phantoms may be relatively heavy, which may make the phantoms difficult for all users to move on and off a patient table each time a calibration scan is carried out. Many phantoms are not ergonomic and may cause user discomfort when lifting or carrying the phantoms.

Thus, embodiments are disclosed herein for a lightweight, ergonomic phantom for calibrating imaging systems such as PCCT systems. The phantom disclosed herein may be comprised of multiple layers of material stacked atop one another and formed into a single-piece phantom. The different layers of the phantom may have different lengths so that different vertical slices of different portions of the phantom may be comprised of different layers of material. A vertical slice containing one or more layers may be referred to as a stack. The entire length of a stack contains the same layers of material. Each stack may be as wide as an X-ray beam. In some examples, the phantom may include a foam cover with integrated handles so that the phantom may be handled easily, while in other examples the phantom may include handles integrated into the base and/or top of the phantom. The foam cover may also cover sharp edges on the phantom, which may make the phantom easier to handle.

The phantom of the present disclosure may include a plug that can couple the phantom to an accessory slot of a patient table of the imaging system. Coupling the phantom to the accessory slot of the patient table allows the phantom to be manipulated by moving the patient table and may allow the phantom to be positioned precisely and consistently within the imaging system. Further, the phantom disclosed herein may be configured to be positioned as close as possible to an X-ray tube during a calibration scan due to the position of the plug on the phantom (thereby allowing the phantom to be positioned relatively close to a bottom of the bore of the imaging system and hence the X-ray tube). By positioning the phantom close to the X-ray tube, the phantom can include thinner layers of material than if the phantom were to be positioned further from the X-ray tube, thereby decreasing the weight of the phantom. Further still, the phantom disclosed herein may have a trapezoidal shape that matches the shape of the X-ray beam, further decreasing the weight of the phantom by dispensing with unnecessary material.

A calibration scan may be performed on the phantom that includes scanning a stack of the phantom, adjusting the position of the table to move the next stack of the phantom into the X-ray beam, and scanning the next stack of the phantom. Precise positioning of the phantom may be especially useful in systems such as PCCT systems that demand frequent calibration, as the calibration scans may be easily replicated. The phantom may further include a visual indicator to signal to users that the phantom is properly installed into the accessory slot of the table.

FIG. 1 illustrates an exemplary PCCT system 100 (also referred to as a photon counting X-ray imaging system) configured for CT imaging with photon counting detectors. Particularly, the PCCT system 100 is configured to image a subject 112 such as a patient, an inanimate object, one or more manufactured parts, and/or foreign objects such as dental implants, stents, and/or contrast agents present within the body. The PCCT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at the same or different energy levels corresponding to the patient. In some embodiments, the X-ray source 104 may enable dual-energy gemstone spectral imaging (GSI) by rapid peak kilovoltage (kVp) switching. In the embodiments described herein, the X-ray detector employed is a photon counting detector which is capable of differentiating X-ray photons of different energies.

In certain embodiments, the PCCT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. In some examples the image processor unit 110 may use an analytic image reconstruction approach such as FBP in addition to an iterative image reconstruction approach.

In some CT imaging system configurations, an X-ray source projects a cone-shaped X-ray radiation beam which is defined with respect to an X-Y-Z Cartesian coordinate system and generally referred to as an "imaging volume." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging volume and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

Figure 2:
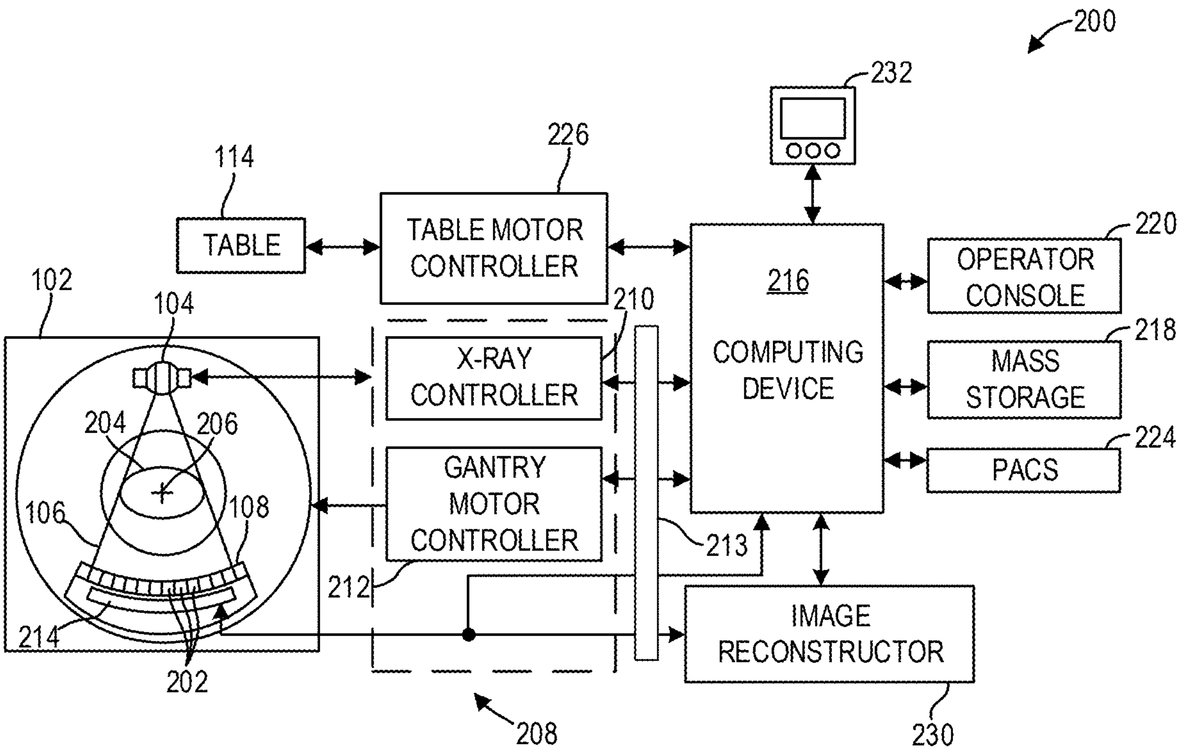
FIG. 2 shows a block schematic diagram of an example CT imaging system, in accordance with one or more embodiments of the present disclosure.

FIG. 2 illustrates an exemplary imaging system 200 similar to the PCCT system 100 of FIG. 1. In accordance with aspects of the present disclosure, the imaging system 200 is configured for imaging a subject 204 (e.g., the subject 112 of FIG. 1). During certain scans, the subject may be a phantom. A phantom may be an object configured to be scanned by the PCCT system as part of a calibration process for the PCCT system. In one embodiment, the imaging system 200 includes the detector array 108 (see FIG. 1). The detector array 108 further includes a plurality of detector elements 202 that together sense the X-ray radiation beam 106 (see FIG. 2) that passes through the subject 204 (such as a patient) to acquire corresponding projection data. In some embodiments, the detector array 108 may be fabricated in a multi-slice configuration including the plurality of rows of cells or detector elements 202, where one or more additional rows of the detector elements 202 are arranged in a parallel configuration for acquiring the projection data. The detector elements 202 may also be referred to as pixels or detector pixels.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where the projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector elements 202 of the detector array 108 may include photon counting detectors which register the interactions of individual photons into one or more energy bins.

The acquired sets of projection data may be used for basis material decomposition (BMD). During BMD, the measured projections are converted to a set of material-density projections. The material-density projections may be reconstructed to form a set of material-density maps or images of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate data from a subset of the detector elements 202 into so-called macro-detectors. The data sampled and digitized by the DAS 214 is transmitted to a computer or computing device 216 via a slip ring 213. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 to generate useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Information may be transmitted between the components residing in the gantry 102 and external devices (such as the computing device 216 and/or image reconstructor 230) via the slip ring 213, which facilitates electronic communication across the rotating gantry. In some examples, the gantry and internal components (e.g., the control mechanism 208, X-ray source 104, the detector array 108) may be collectively defined as a PCCT scanner, and as such the computing device 216 and image reconstructor 230 may reside off the scanner.

Figure 3:
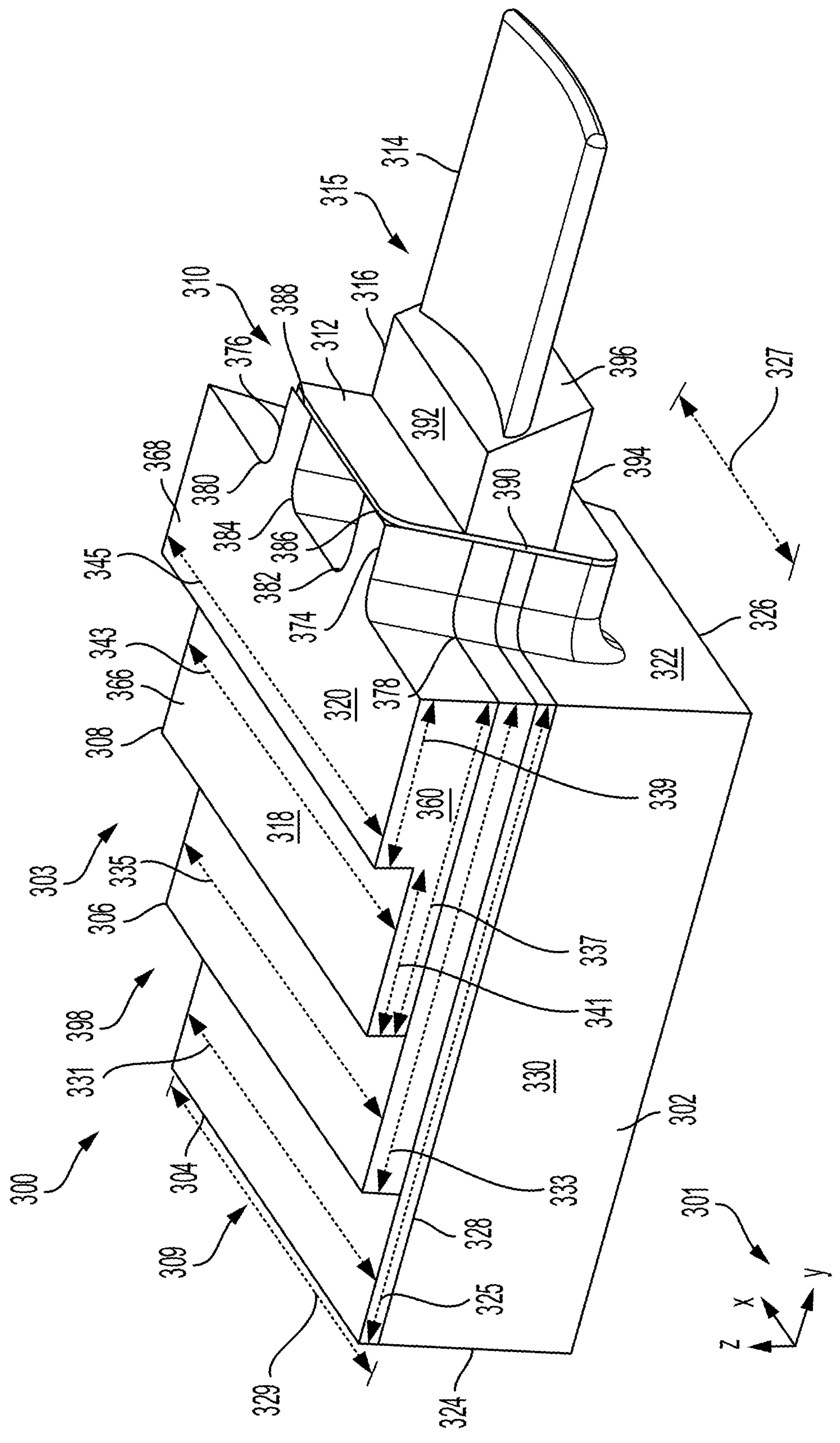
FIG. 3 is a perspective view of a phantom according to a first embodiment of the disclosure.
Figure 4:
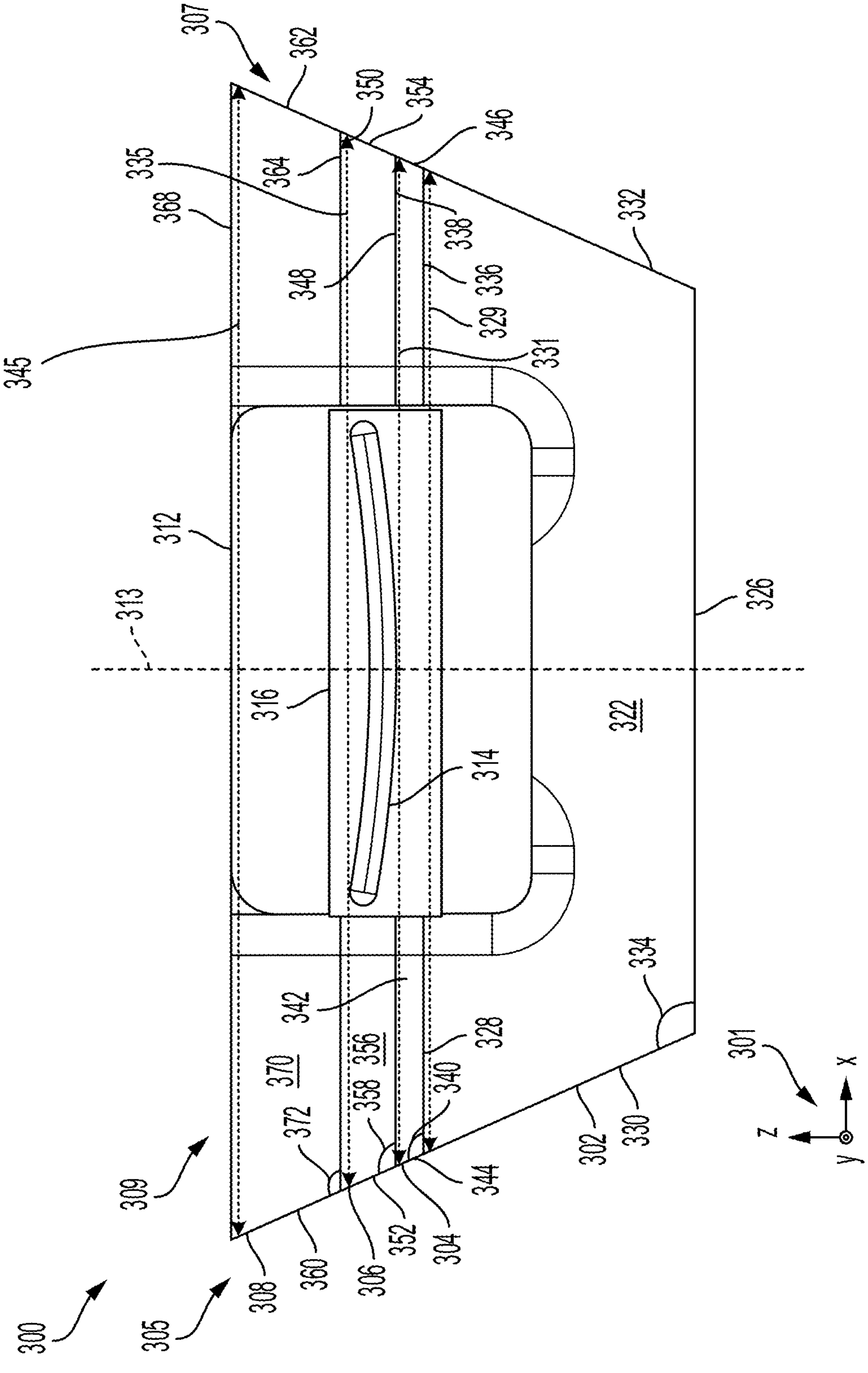
FIG. 4 is a front view of the phantom of FIG. 3.
Figure 5:
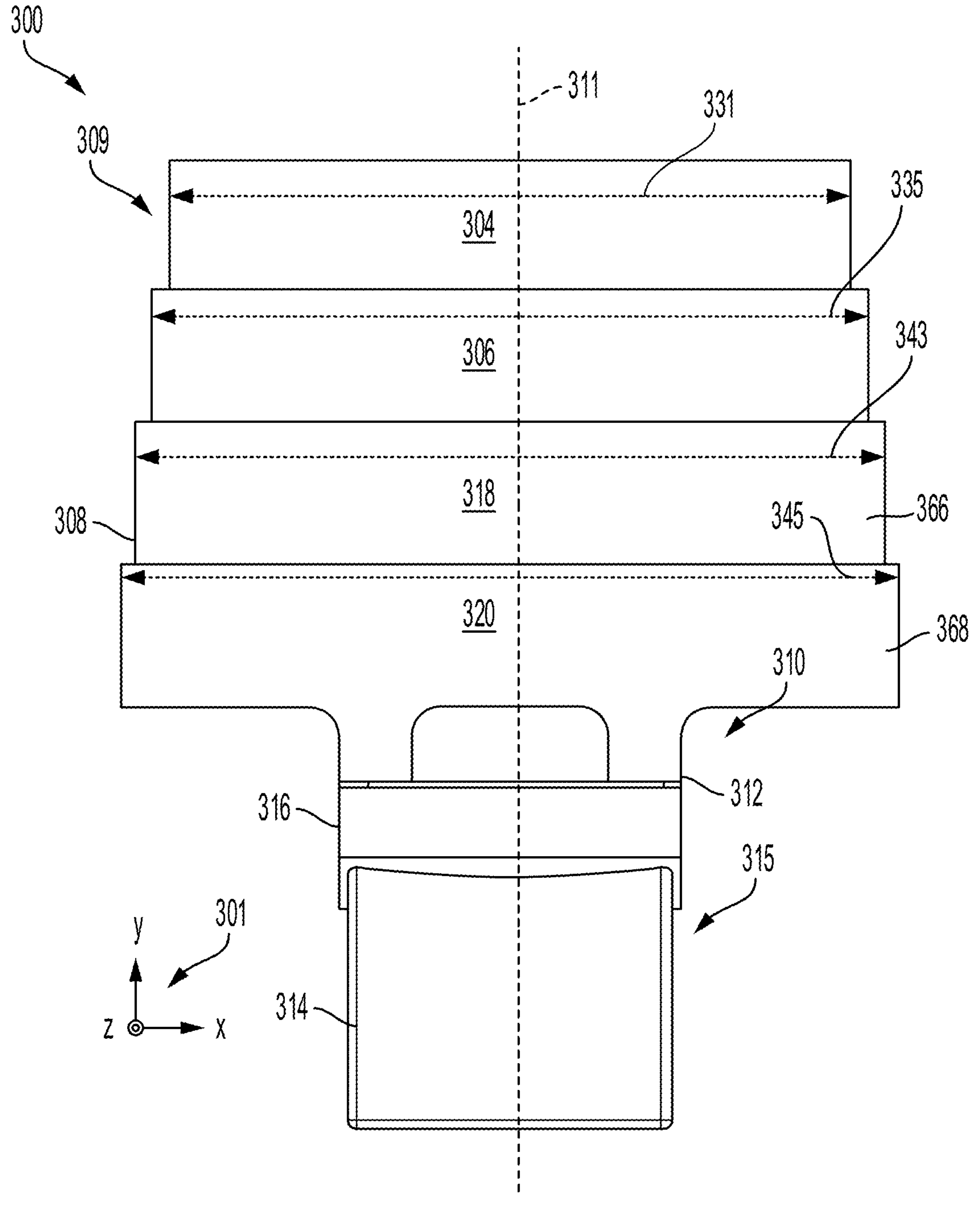
FIG. 5 is a top view of the phantom of FIG. 3.

FIG. 3 is a perspective view of an example of a phantom 300, FIG. 4 is a front view of the example phantom 300, and FIG. 5 is a top view of the example phantom 300 and as such FIGS. 3, 4 and 5 may be described collectively. Each of FIGS. 3-5 includes a Cartesian coordinate system 301. The z-axis of coordinate system 301 may be a vertical axis (e.g., parallel to a gravitational axis), the y-axis of coordinate system 301 may be a longitudinal axis (e.g., horizontal axis), and/or the x-axis of coordinate system 301 may be a lateral axis, in one example. However, the axes may have other orientations, in other examples. When referencing direction, positive may refer to in the direction of the arrow of the x-axis, y-axis, and z-axis and negative may refer to in the opposite direction of the arrow of the x-axis, y-axis, and z-axis. A filled circle may represent an arrow and axis facing toward, or positive to, a view. An unfilled circle may represent an arrow and an axis facing away, or negative to, a view. Further, FIGS. 3-8 and 13 are drawn to scale, though other relative dimensions could be used if desired.

Figure 10:
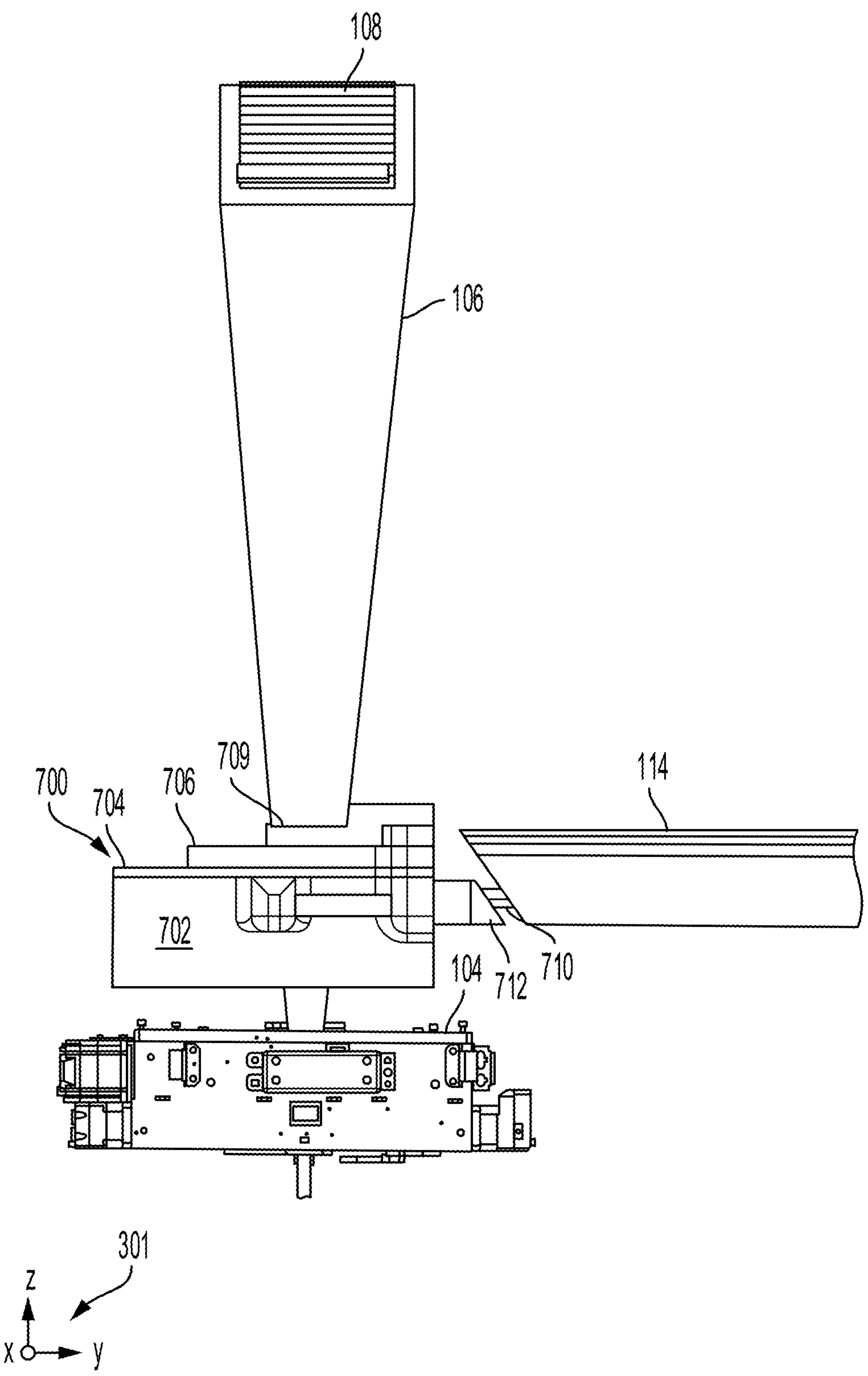
FIG. 10 is a side view of the phantom of FIG. 7 positioned within a CT imaging system.
Figure 11:
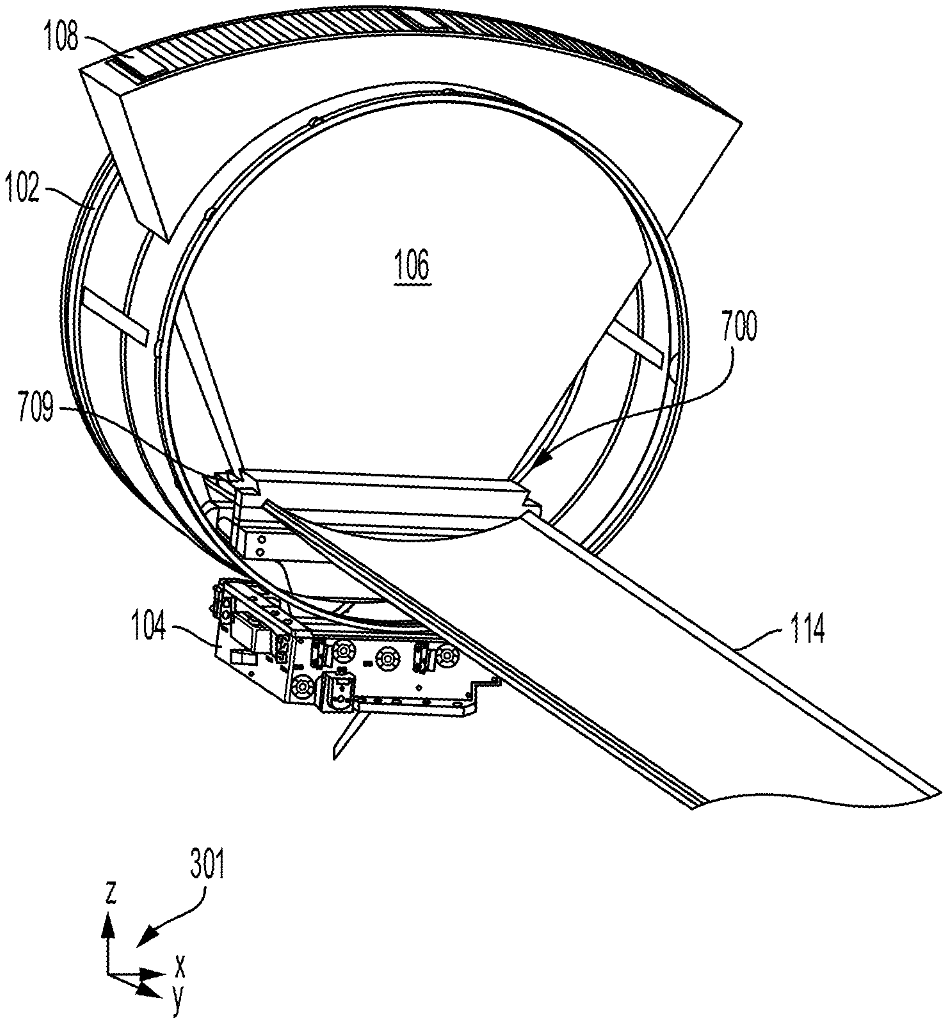
FIG. 11 is a perspective view of the phantom of FIG. 7 positioned within the CT imaging system.

The phantom 300 may be comprised of a main body 303, a plug section 315, and a coupling section 310 that couples the plug section 315 to the main body 303. The main body 303 may be a trapezoidal prism in shape. However, in other examples, the phantom 300 may include a main body that is a different shape than main body 303, such as a rectangular prism or a cylinder. The main body 303 may include a base 302 made of a first material, such as PVC, upon which a plurality of layers of different material (e.g., PVC and PE) are positioned. The trapezoidal shape of the main body 303 may allow each layer to match the width of the X-ray beam at the height of each layer, when the phantom 300 is positioned in a gantry of an imaging system and the X-ray tube is positioned below the phantom, as shown in FIGS. 10 and 11 and described in more detail below. The X-ray beam expands as it extends from the X-ray source, and thus the top layers of material of the main body 303 may be struck by a wider X-ray beam than the lower layers of material (e.g., the base 302) of the main body 303. In the example shown in FIG. 3, the plurality of layers includes a first layer 304, a second layer 306, and a third layer 308 arranged atop the base 302. The plurality of layers may be comprised of the first material and a second material (e.g., PE). The layers may be made of PVC, PE, or another material. For example, the first layer 304 may be comprised of PE, the second layer 306 may be comprised of PVC, and the third layer may be comprised of PE. However, the layers may be made of any combination of materials in any order. In some examples, the layers may all be made of the same material.

The main body 303 of the phantom 300 may include a top 398 (e.g., a top surface) and a base bottom 326 (e.g., a bottom surface). The top 398 may have a stepped profile comprised of the plurality of layers of material (which in some examples may include at least two different materials). A longitudinal axis 311 extends along the y axis of a Cartesian coordinate system 301 and the phantom 300 may be symmetrical about the longitudinal axis 311. There may be a vertical axis 313 that extends along the z axis of the Cartesian coordinate system 301 and the phantom 300 is symmetrical about the vertical axis 313. The main body 303 of the phantom 300 may have a front 309, a back (not shown), a first side 305, and a second side 307. The first side 305 and the second side 307 may be comprised of side faces of the base 302 and the side faces of the plurality of layers of material stacked upon the base 302. The base bottom 326 may be narrower than the top 398. The first side 305 and the second side 307 may extend away from the vertical axis 313 at an angle that is larger than 90 degrees (e.g., a 120-degree angle) from the base bottom 326 to the top 398. In one example, the phantom 300 may measure between 5 mm and 400 mm along the z-axis, between 20 mm and 450 mm along the y-axis, and between 250 mm and 650 mm along the x-axis of the Cartesian coordinate system 301.

The base 302 may be a trapezoidal prism with a base front 322 and a base back 324 that are trapezoidal in shape. The base 302 may have the base bottom 326 and a base top 328 that may each be rectangular in shape. The base bottom 326 may have a narrower width along the x-axis than the base top 328 but the base bottom 326 and the base top 328 may share the same length along the y-axis. For example, the base bottom 326 and the base top 328 may have a first length 325. Likewise, the base bottom 326 may have a first width 327, and the base top 328 may have a second width 329. The first width 327 may be greater than the second width 329. The base 302 may have a first base side 330 and a second base side 332. In the illustrated example, the first base side 330 and the second base side 332 may each be rectangular surfaces that extend at a 120-degree angle 334 from the base bottom 326 to the base top 328. Likewise, the first base side 330 and the second base side 332 may couple the base front 322 to the base back 324. In the example that the main body 303 is trapezoidal in shape, the trapezoidal shape of the phantom 300 may reduce weight (e.g., when compared to a square phantom large enough to encompass the beam). However, in other embodiments, the phantom may be another shape, such as square, rectangular, circular, etc. in shape.

The first layer 304 is coupled to the base top 328. The first layer 304 may be a trapezoidal prism. The first layer may have a first layer bottom 336 and a first layer top 338. The first layer bottom 336 may be identical in shape and size to the base top 328, and the first layer top 338 may be a rectangle identical in length to the first layer bottom 336 but wider than the first layer bottom 336. For example, the first layer bottom 336 and the first layer top 338 may each have the first length 325. The first layer bottom 336 may have the second width 329. Likewise, the first layer top 338 may have a third width 331. The third width 331 may be greater than the second width 329. The first layer bottom 336 is in face sharing contact with the base top 328 along the entire extent of each of the first layer bottom 336 and the base top 328. The first layer 304 may have a first layer front 342 and a first layer back (not shown) that are connected by a first layer first side 344 and a first layer second side 346. The first layer first side 344 and the first layer second side 346 may couple the first layer front 342 to the first layer back and the first layer top 338 to the first layer bottom 336. The first layer first side 344 and the first layer second side 346 may be identical rectangular planes and be arranged at an angle 340 from the first layer bottom 336.

The second layer 306 may be arranged above the first layer 304. The second layer 306 may be made of a different material than the first layer 304, at least in some examples. The second layer 306 is a trapezoidal prism that may be shorter in length than the first layer 304. However, in some examples, the second layer 306 may be equal in length to the first layer 304. The second layer 306 may have a second layer bottom 348 and a second layer top 350 that are rectangles with the same length. The second layer bottom 348 may be identical in width to the first layer top 338. The second layer bottom 348 is in face sharing contact with the first layer top 338 along the entire extent of each of the second layer bottom 348 and the first layer top 338. The second layer top 350 may be wider than the second layer bottom 348. For example, the second layer bottom 348 and a second layer top 350 may each have a second length 333. The second layer bottom 348 may have the third width 331. Likewise, the second layer top 350 may have a fourth width 335. The fourth width 335 may be greater than the third width 331. The second layer 306 may have a second layer front 356 and a second layer back (not shown) which may be two identical trapezoidal faces. The second layer may have a second layer first side 352 and a second layer second side 354. The second layer first side 352 and the second layer second side 354 may couple the second layer bottom 348 to the second layer top 350 and the second layer front 356 to the second layer back. The second layer first side 352 and the second layer second side 354 may extend from the second layer bottom 348 at an angle 358 that is identical to angle 340 and angle 334. In the example phantom 300 shown in FIG. 3, the base 302 has a first height along the z axis and the first layer 304 has a second height along the z axis that is less than the first height. The second layer 306 has a third height that is greater height than second height of the first layer 304 but less than the first height of the base 302. However, in other examples, the second layer 306 may have a greater height than the first layer 304, or be equal in height to the first layer 304.

The third layer 308 may be arranged above the second layer 306 and may be made of a different material from the first layer 304 and/or the second layer 306, at least in some examples. The third layer 308 may have a stepped side profile, comprised of a first L-shaped side 360 and a second L-shaped side 362. The third layer 308 include a first step 318 and a second step 320. In the example phantom 300, the third layer 308 is shorter in length than the second layer 306. The third layer 308 may include a third layer front 370 and a third layer back (not shown) which may be trapezoidal in shape. The third layer 308 may include a third layer bottom 364, a first step top 366, and a second step top 368. The third layer bottom 364 may have an identical width to the second layer top 350 and may have a length 337 that is shorter than the second layer top 350. The first step top 366 and the second step top 368 may each be rectangles half of the length of the third layer bottom 364. For example, the first step top 366 may have a length 341 and the second step top 368 may have a length 339. The second step top 368 may be wider than the first step top 366. For example, the third layer bottom 364 may have the fourth width 335, the first step top 366 may have a fifth width 343, and the second step top 368 may have a sixth width 345. The sixth width 345 may be greater than the fifth width 343, and the fifth width 343 may be greater than the fourth width 335. The third layer 308 may have a fourth height (from the third layer bottom 364 to the second step top 368) that is greater than the second height and the third height but less than the first height, though in other examples, the fourth height may be equal to the second or third height, less than the third height, or be another suitable height. The first L-shaped side 360 and the second L-shaped side 362 may couple the third layer bottom 364 to the first step top 366, the second step top 368, the third layer front 370, and the third layer back. The first L-shaped side 360 and the second L-shaped side 362 may extend at an angle 372 from the third layer bottom 364.

In some examples, the base 302, the first layer 304, the second layer 306, and the third layer 308 may be fused at the planes of contact between each layer. For example, the phantom 300 may be injection molded. In other examples, the base 302, the first layer 304, the second layer 306, and the third layer 308 may be formed separately and then coupled together using adhesive, heat, and/or another coupling mechanism. In one examples, the layers may be joined by fasteners, such as bolts, located outside of the path of the X-ray beam. In other examples, the layers may be joined by features such as a press fit or interface fit, a tongue and groove fit, or adhesive applied between the layers.

According to the description above, the top 398 of the phantom 300 may be stepped in profile based on the diminishing lengths of the first layer 304, the second layer 306, and the third layer 308. Each step may comprise a stack, which may be a vertical section of the phantom 300 that includes the material of that step. The phantom 300 may include a first vertical stack that includes the base 302 and the first layer 304; a second vertical stack that includes the base 302, the first layer 304, and the second layer 306; a third vertical stack that includes the base 302, the first layer 304, the second layer 306, and a first step 318 of the third layer 308; and a fourth vertical stack that includes the base 302, the first layer 304, the second layer 306, and a second step 320 of the third layer 308. However, in the example that one or more of the first layer, 304, second layer 306, and third layer 308 share the same length, the composition of the vertical stacks may be different. For example, if the second layer 306 had the same length as the first layer 304 the first stack would include the base 302, the first layer 304, and the second layer 306.

The coupling section 310 of the phantom 300 may include a first arm 374, a second arm 376, and a fastening plate 312. Each of the first arm 374 and the second arm 376 may comprise extensions of the base 302, the first layer 304, the second layer 306, and the third layer 308 (e.g., that extend from the front of each layer and extend from the main body 303 of the phantom 300). The first arm 374 and the second arm 376 may be identical, and may extend a specific distance from the front face of each layer of the main body and each arm may have a specific width. The first arm 374 and the second arm 376 may have flat rectangular tops that are integrated into the second step 320. The first arm 374 and the second arm 376 may extend outward from the entire vertical extent of the first layer 304, the second layer 306, and the third layer 308 and may extend outward from a portion of the base 302. The first arm 374 may intersect the front face of each layer of the main body at a first rounded corner 378 and a second rounded corner 382. The second arm 376 may intersect the front face of each layer of the main body at a third rounded corner 380 and a fourth rounded corner 384. The corners may be rounded to allow an operator to interact with the arms without exposing the operator to sharp corners. The first arm 374 and the second arm 376 may be separated by an opening. The first arm 374 may have a first arm front 386 which may be a rectangular face that extends the height of the first arm 374. The second arm 376 may have a second arm front 388 which may be a rectangular face that extends the height of the second arm 376. The first arm front 386 and the second arm front 388 may lie in the same z-x plane.

The fastening plate 312 may be coupled to the first arm front 386 and the second arm front 388. The fastening plate 312 may have a rectangular shape with rounded corners. The fastening plate 312 may have a width equal to the span from the first arm 374 to the second arm 376 and a height equal to the height of the first arm 374 and the second arm 376. The plug section 315 may include a plug base 316 affixed to the fastening plate 312 and a plug 314 that extends outward (e.g., in the −y direction) from the plug base 316. The plug base 316 may be a trapezoidal prism with a vertical side 390 in contact with the fastening plate 312. The vertical side 390 may be identical in width to the fastening plate 312, and may be affixed in the center of the fastening plate 312 according to the height of the fastening plate 312. The vertical side 390 may have a specific height along the z-axis. The plug base 316 may have a plug bottom 394 and a plug top 392. The plug bottom 394 and the plug top 392 may be as long along the x-axis as the fastening plate 312 but the plug bottom 394 may be wider along the y-axis than the plug top 392. The plug base 316 may further include a slanted side 396 that may couple the plug bottom 394 to the plug top 392. The plug 314 may extend from the slanted side 396. The plug 314 may be arc shaped and have a specific length, width, and radius of curvature to couple to an accessory slot of a patient table (e.g., the length, width, thickness, and radius of curvature may match/be complementary to the accessory slot of the patient table so that the plug 314 may be slidingly received by the accessory slot and secured via a locking mechanism of the accessory slot).

Figure 6:
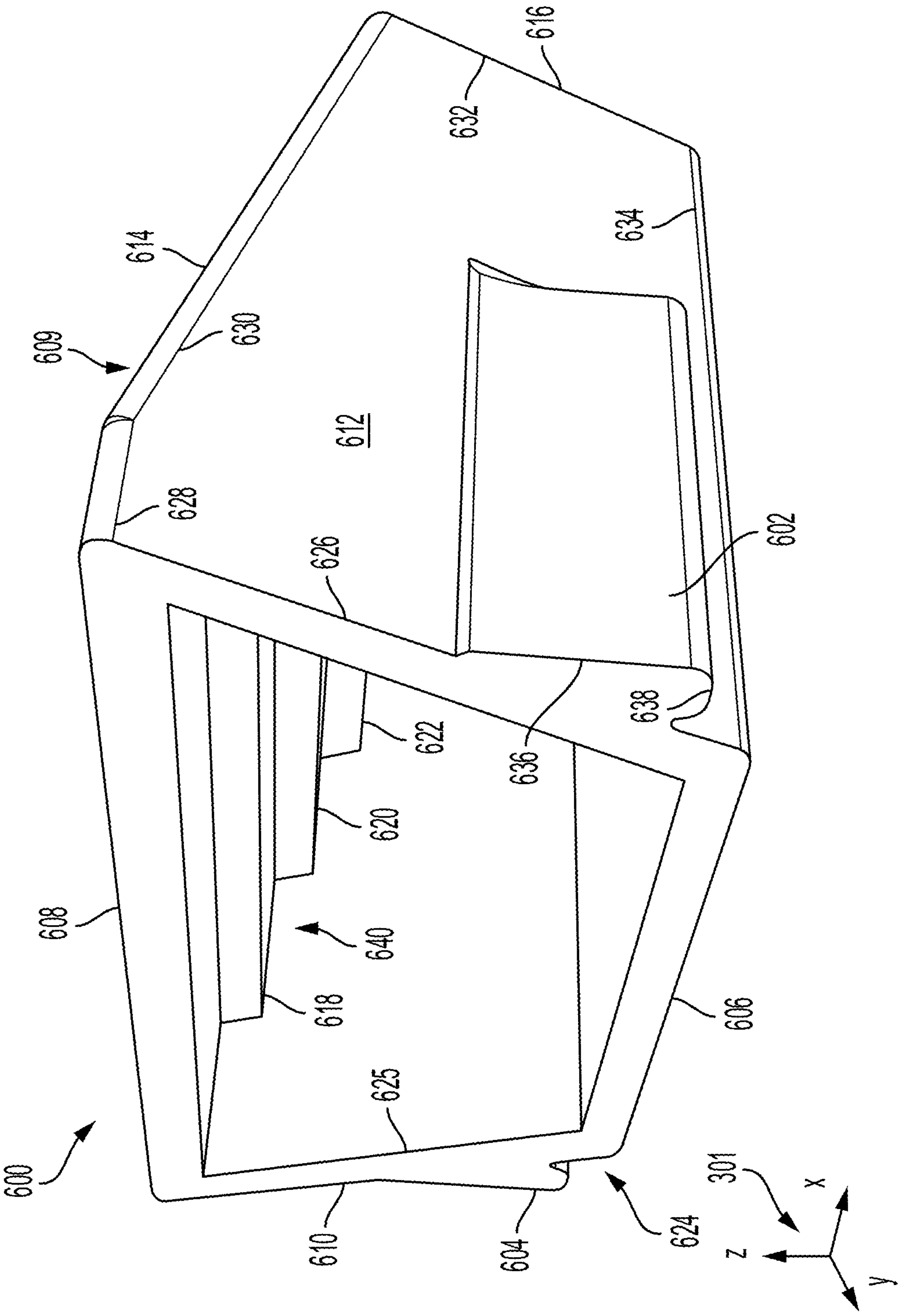
FIG. 6 is a perspective view of a cover for a phantom according to embodiments of the disclosure.

FIG. 6 is perspective view of a cover 600 for a phantom, such as phantom 300. The cover 600 may be made out of a foam material to protect the phantom 300 from degradation as well as cover any edges of the phantom 300 to facilitate easier handling/moving of the phantom 300. The phantom 300 may be inserted into the cover 600 to couple the phantom 300 to the cover 600. The cover 600 may include a bottom 606, a first side 610, a second side 612, a top 609 comprised of a flat top portion 608 and a slanted top portion 614, and a cover front 624. Each of the bottom 606, the first side 610, the second side 612, and the top 609 includes an outer surface that faces the environment and an inner surface that faces a hollow interior of the cover 600. The bottom 606 may be a flat, rectangular piece of foam in the x-y plane. The bottom 606 may be sized to accommodate the base bottom 326 (e.g., the inner surface of the bottom 606 may have a length and width that match the length and width of the base bottom 326, with a small tolerance to allow movement of the phantom in and out of the cover). The first side 610 and the second side 612 may extend away from the bottom 606 at a 120-degree angle. The first side 610 and the second side 612 may be identical irregular pentagons that may be constructed out of foam. More features of the second side 612 are visible in FIG. 6 than of the first side 610, however the two sides are identical and therefore the description of the features of the second side 612 may also apply to similar features on the first side 610.

The second side 612 may be defined by a front edge 626, a first top edge 628, a second top edge 630, a back edge 632, and a bottom edge 634. The first top edge 628 may be a straight edge where the second side 612 is coupled to the flat top portion 608. The second top edge 630 is a straight edge where the second side 612 is coupled to the slanted top portion 614. The second top edge 630 may be angled in the −z direction. The back edge 632 may be a straight edge where the second side 612 is coupled to the cover back 616.

The front edge 626 may be a straight edge that forms part of the cover front 624. The front edge 626 may further include a handle edge 636 that extends from the front edge 626 in the x direction to form a second handle 602. The second handle 602 may extend from the second side 612 of the cover 600. The second handle 602 may have a width along the x axis suitable for a person to grip the second handle 602. and may include a rounded edge 638 at the bottom. The rounded edge 638 may extend from the surface of the second side 612 to form a gap configured to accommodate fingers of a user when moving the cover 600. The first side 610 may have a first handle 604. When the phantom 300 is inserted into the cover 600, the first handle 604 and the second handle 602 may be used together by one or more people to lift and move the phantom 300 and the cover 600.

The top 609 of the cover 600 may include the flat top portion 608 that is a rectangular piece of foam that extends in the x-y plane between the tops of the first side 610 and the second side 612. The flat top portion 608 may be coupled to the slanted top portion 614. The slanted top portion 614 may be rectangular piece of foam that is also coupled to the first side 610, and the second side 612. The cover 600 may have a cover back 616, that may be open. The cover back 616 may be an opening defined by the slanted top portion 614, the first side 610, the second side 612, the bottom 606, and the slanted top portion 614. In some examples, the cover back 616 may be closed and the cover back 616 may include a flat, rectangular piece of foam that is coupled to the first side 610, the second side 612, the bottom 606, and the slanted top portion 614. It is to be appreciated that each of the pieces of foam described herein may separate pieces that have been joined together, or the cover 600 may be molded or otherwise formed such that the cover 600 is comprised of one single piece of material. In such cases, the different pieces described herein may not be separate pieces.

The cover front 624 may include a planar front surface that extends between an outer peripheral edge (defined by the outer edges of the bottom 606, the first side 610, the second side 612, and the flat top portion 608) and an inner peripheral edge 625 that is comprised of inner edges of the bottom 606, the first side 610, the second side 612, and the flat top portion 608. The space within the inner peripheral edge 625 may define a front opening of the cover 600. The cover front 624 may thus be open to the hollow interior of the cover 600. The inner surface of the top 609 (e.g., the inner surfaces of the flat top portion 608 and the slanted top portion 614) may form a roof 640 of the interior of the cover 600. The roof 640 may include a plurality of rectangular projections that extend from the roof 640 to match the stepped top of the phantom 300 comprised of the first layer 304, the second layer 306, the first step 318, and the second step 320. The plurality of projections may include a first rectangular projection 618, a second rectangular projection 620, and a third rectangular projection 622. The first rectangular projection 618 may be shaped to conform to the space between the second step 320 and the first step 318 when the phantom 300 is inserted into the cover 600. The first rectangular projection 618 may be in face sharing contact with the first step 318 when the phantom 300 is housed in the cover 600. The second rectangular projection 620 may be shaped to conform to the space between the first step 318 and the second layer 306 when the phantom 300 is inserted into the cover 600. The second rectangular projection 620 may be in face sharing contact with the second layer 306 when the phantom 300 is housed in the cover 600. The third rectangular projection 622 may be shaped to conform to the space between the second layer 306 and the first layer 304 when the phantom 300 is inserted into the cover 600. The third rectangular projection 622 may be in face sharing contact with the first layer 304 when the phantom 300 is housed in the cover 600.

Thus, the interior of the cover 600 may have a shape that matches (e.g., is complementary to) the outer shape of the main body 303 of the phantom 300 and is configured to house the main body 303 of the phantom 300 in face-sharing contact fashion. In the example that one or more of the layers of the phantom, such as the first layer 304, the second layer 306 or the third layer 308, are of the same length, the top of the phantom may have a different profile than that of the phantom 300. In that example, the shape of the interior of the cover may be adjusted to be in face sharing contact with the adjusted shape of the top of the phantom. Likewise, if the phantom has a rectangular shape rather than a trapezoidal shape, the interior and the exterior of the cover 600 may be adapted to match the shape of the phantom, and thus the first side and the second side of the cover 600 may be straight instead of slanted. The cover 600 may be comprised of a lightweight yet sturdy material, such as foam, and may have sufficient flexibility or sizing tolerance to allow insertion and removal of the phantom 300.

Figure 13:
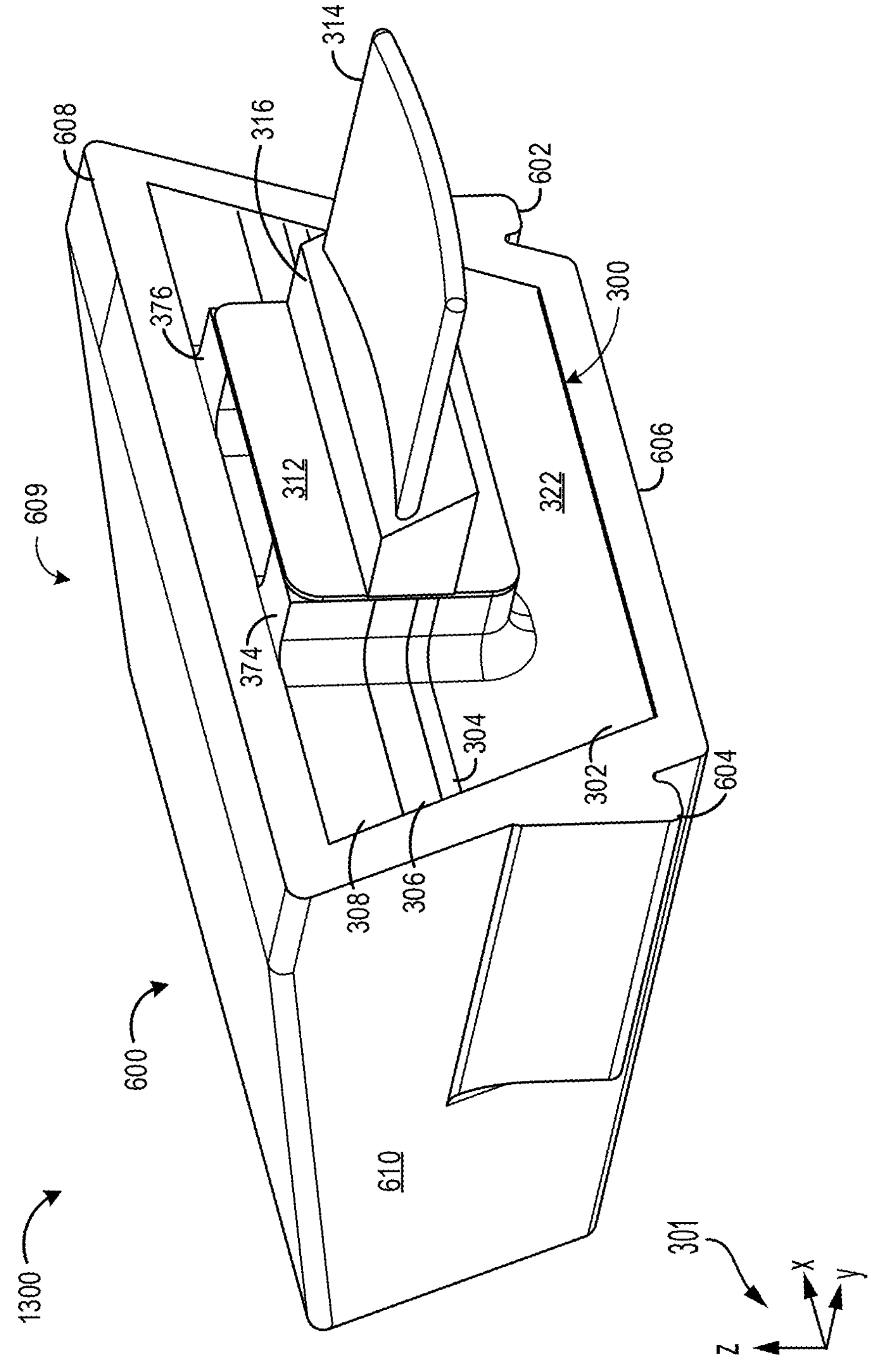
FIG. 13 is a perspective view of the phantom of FIG. 3 coupled to the cover of FIG. 6.

FIG. 13 is a perspective view 1300 of the phantom 300 housed within the cover 600. As shown in FIG. 13, when housed in the cover 600, the front surfaces of the various layers of the main body 303 of the phantom 300 (e.g., the base front 322, the first layer front 342, the second layer front 356, and the third layer front 370) may lie in the same plane as the planar front surface of the cover front 624. The first arm 374 and the second arm 376 as well as the plug base 316 and plug 314 may extend out of the cover 600. In other examples, the front surfaces may be slightly recessed in the hollow interior of the cover 600. In the example that the front surfaces are slightly recessed into the hollow interior of the cover 600, a portion of the first arm 374 and the second arm 376 may also be recessed into the hollow interior of the cover 600. However, the plug base 316 and the plug 314 as well as a portion of the first arm 374 and the second arm 376 may extend out of the cover 600. The cover 600 may thereby protect a user from touching the edges of the phantom 300 and facilitate easier moving of the phantom 300 via the handles on either side of the cover 600. In some examples, the cover 600 may be comprised of radiolucent material so that the cover 600 may be left in place over the phantom 300 during a calibration scan. In other examples, the cover 600 may be removed during scanning (e.g., the cover 600 may be removed from the phantom 300 once the plug 314 has been secured to the patient table). Phantom 300 includes a main body that is a trapezoidal prism in shape. However, in other examples, a phantom may have an alternative shape, such as a cylinder, a cube, a rectangular prism, or other shapes. In the example that the main body of the phantom is a rectangular prism, the phantom may have a flat rectangular front and back that are identical in size and shape, as well as two identical flat rectangular sides, and a flat rectangular bottom. The top of the phantom may be a rectangle of the same area as the bottom with a stepped profile of layers stacked atop a base, as described above. The layers may all have the same width and have straight sides at right angles from the respective bottoms of the layers to maintain the rectangular shape of the main body of the phantom. In the example that the main body of the phantom is a rectangular prism, the cover may be shaped to couple to the phantom. The cover may be similar in construction to cover 600, but adapted to couple to the rectangular phantom. The cover may have two identical rectangular sides that include handles. The rectangular sides may be affixed at right angles to a rectangular bottom. The cover may include a top that is affixed at right angles to the sides of the cover. The top of the cover may include a flat portion and a slanted portion similar to the top 609 of the cover 600. The top of the cover may have a stepped profile in the interior to match the contours of the top of the phantom. The front of the cover may be a rectangular aperture through which the rectangular phantom may be inserted. The back of the phantom may be a rectangular aperture.

Figure 7:
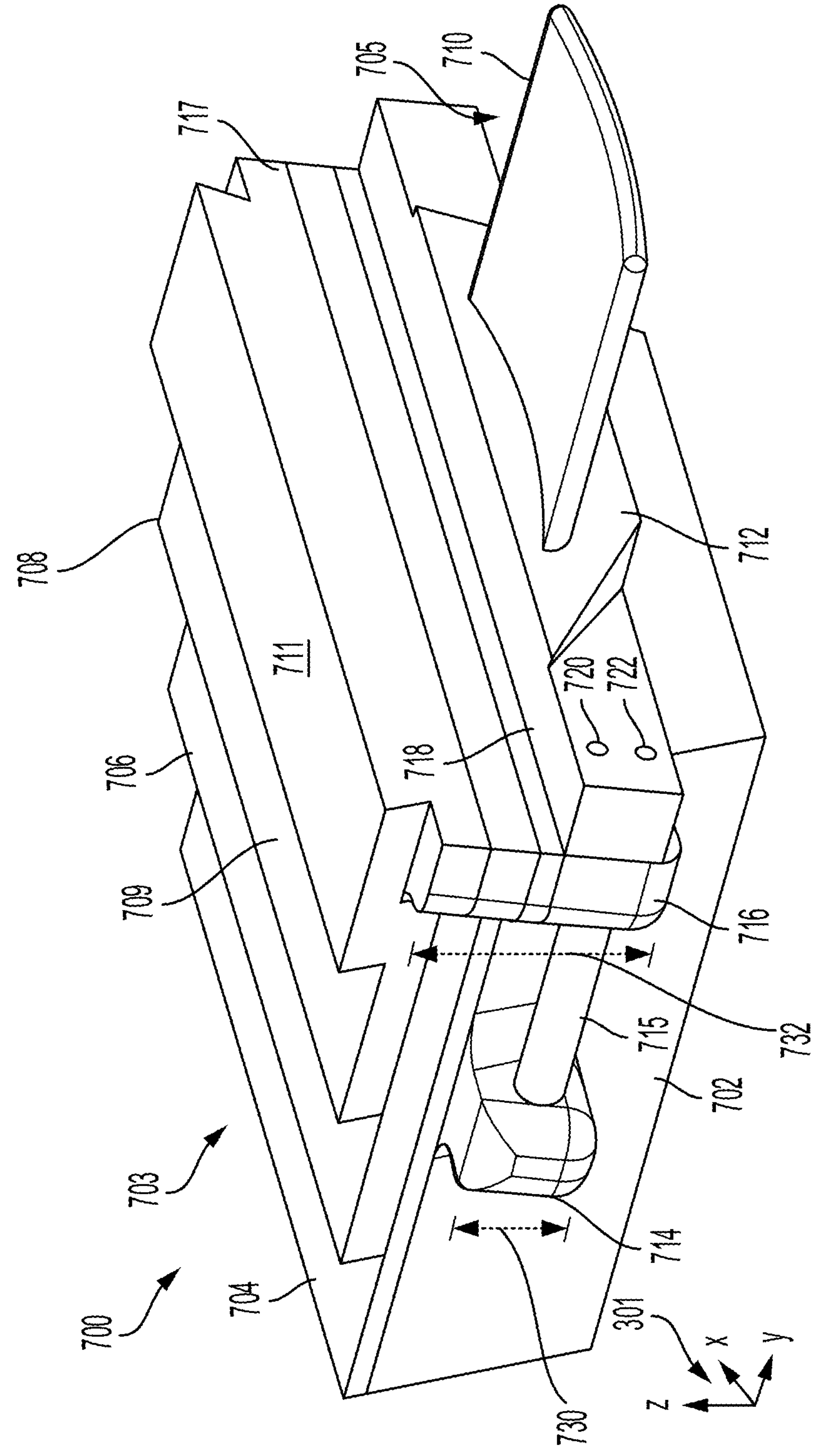
FIG. 7 is a perspective view of a phantom according to a second embodiment of the disclosure.

FIG. 7 is a perspective view of a phantom 700 according to a second embodiment of the disclosure. Phantom 700 is similar to the phantom 300 described with respect to FIGS. 3-5 in that the phantom 700 includes a main body 703 comprising a base 702 with three layers of PVC, PE, and/or another material stacked atop the base 702. The phantom 700 may include a first layer 704, a second layer 706, and a third layer 708 comprised of a first step 709 and a second step 711. The phantom 700 may further include a plug portion 705 comprising a plug 710 and a plug base 712. The plug 710 and plug base 712 may be similar to the plug 314 and the plug base 316, respectively. The phantom 700 may be identical to the phantom 300 except for the differences described below.

The phantom 700 includes handles integrated into the base 702 rather than a cover such as cover 600. FIG. 7 shows a handle 715 coupled to the base 702 by a first fastening protrusion 714 and a second fastening protrusion 716. The handle 715 may be a cylinder made of the same material as the base 702. The first fastening protrusion 714 may be a rectangular extension of the base 702 with a rounded front face. The first fastening protrusion 714 may be coupled to the handle 715. The second fastening protrusion 716 may have a greater height than the first fastening protrusion 714. For example, the first fastening protrusion 714 may have a first height 730 and the second fastening protrusion 716 may have a second height 732. The second height 732 may be greater than the first height 730. The second fastening protrusion 716 may be a rounded protrusion that includes a rounded protrusion of the base 702, the first layer 704, the second layer 706, and the third layer 708 stacked atop one another. The handle 715 may be coupled to the portion of the second fastening protrusion 716 that is formed out of the base 702. The handle 715 is coupled to the first fastening protrusion 714 and the second fastening protrusion 716 at the same height. The phantom 700 may include an identical handle and fastening protrusions on the opposite side of the phantom 700. For example, a fourth fastening protrusion 717 is shown extending out from on the opposite side of the phantom 700 as the handle 715. While not shown in FIG. 7, it is to be appreciated that a third fastening protrusion, similar to the first fastening protrusion 714, and a second handle, similar to the handle 715, are likewise included on the opposite side of the phantom 700.

Additionally, the phantom 700 does not include a first arm or a second arm, such as the first arm 374 and the second arm 376 of phantom 300, and the phantom 700 does not include a fastening plate such as the fastening plate 312 of the phantom 300. Instead, the phantom 700 includes a rectangular coupling base 718 that is coupled to the plug base 712. The rectangular coupling base 718 may be made of the same material as the plug base 712 and is a rectangular prism that spans the width of the phantom 700 including the second fastening protrusion 716 and the fourth fastening protrusion 717. The rectangular coupling base 718 may be fastened to the second fastening protrusion 716 by a first fastener 720 and a second fastener 722. The first fastener 720 and the second fastener 722 may be a screw, bolt, or another fastener. The rectangular coupling base 718 presents an alternative attachment site for the plug base compared to the first arm 374 and the second arm 376 included in the phantom 300. In some examples, the rectangular coupling base 718 may be included on phantom 300 rather than the coupling arms and plate described above.

Figure 8:
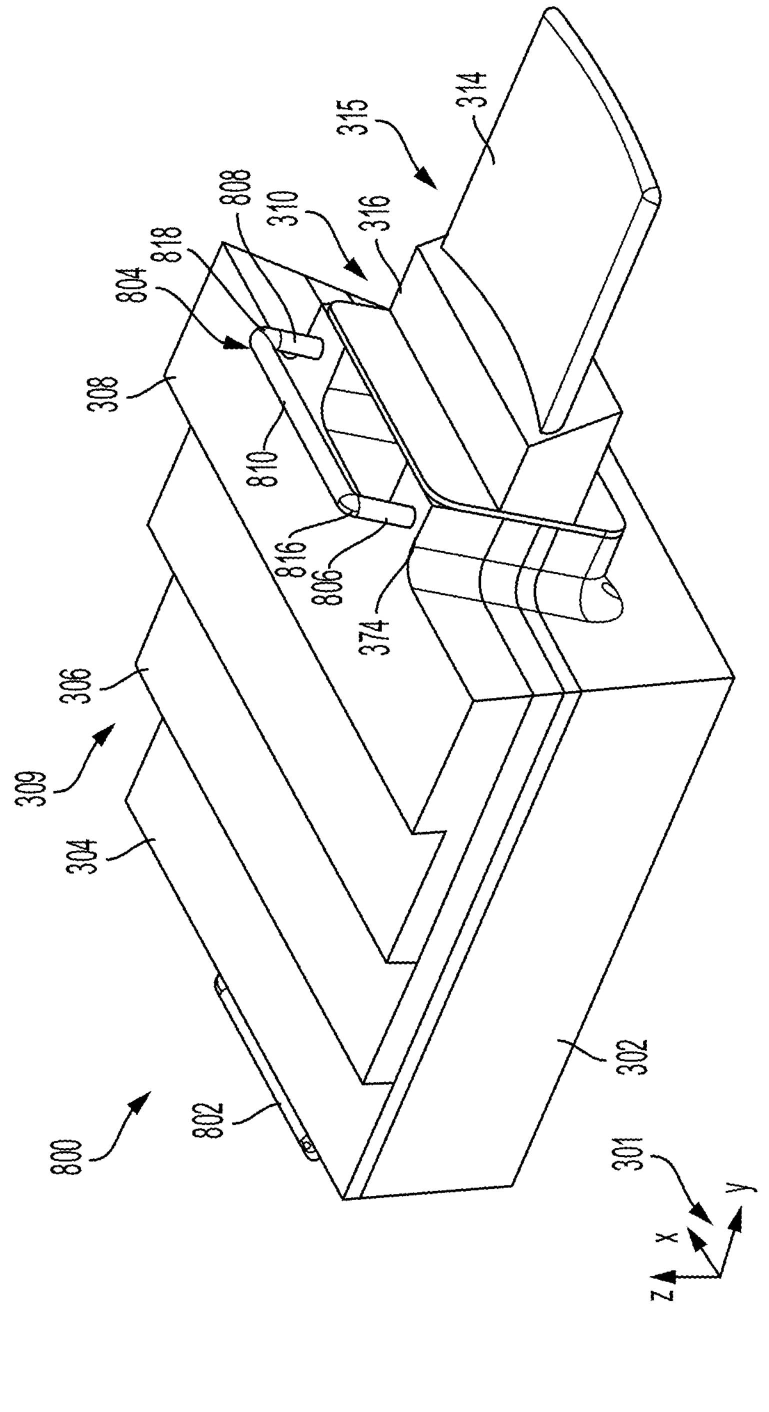
FIG. 8 is a perspective view of a phantom according to a third embodiment of the disclosure.

FIG. 8 is a perspective view of a phantom 800 according to a third embodiment of the disclosure. The phantom 800 is identical to the phantom 300 described with respect to FIGS. 3-5 with the exception of inclusion of a first handle 802 and a second handle 804. The second handle 804 may comprise a first cylinder 806, a second cylinder 808, and a third cylinder 810. The first cylinder 806 may extend in the positive z direction from the first arm 374 of the phantom 800 and the second cylinder 808 may extend in the positive z direction from the second arm 376 of the phantom 800. The first cylinder 806 and the second cylinder 808 may be identical in height and diameter and may be coupled at a right angle to the third cylinder 810 by rounded corners. For example, the first cylinder 806 may be connected to the third cylinder 810 via a first rounded corner 816. The second cylinder 808 may be connected to the third cylinder 810 via a second rounded corner 818. The third cylinder 810 may be identical in diameter to the first cylinder 806 and the second cylinder 808 and may have a length that spans the distance between the first cylinder 806 and the second cylinder 808. The first handle 802 may be substantially similar to the second handle 804 (e.g., the first handle 802 may include two cylinders extending outward in the −y direction and a third cylinder coupled between the two cylinders) and may be coupled to the center of the back 324 of the phantom 800. The first handle 802 and the second handle 804 may allow the phantom 800 to be easily picked up and handled without a cover such as cover 600.

Figure 9A:
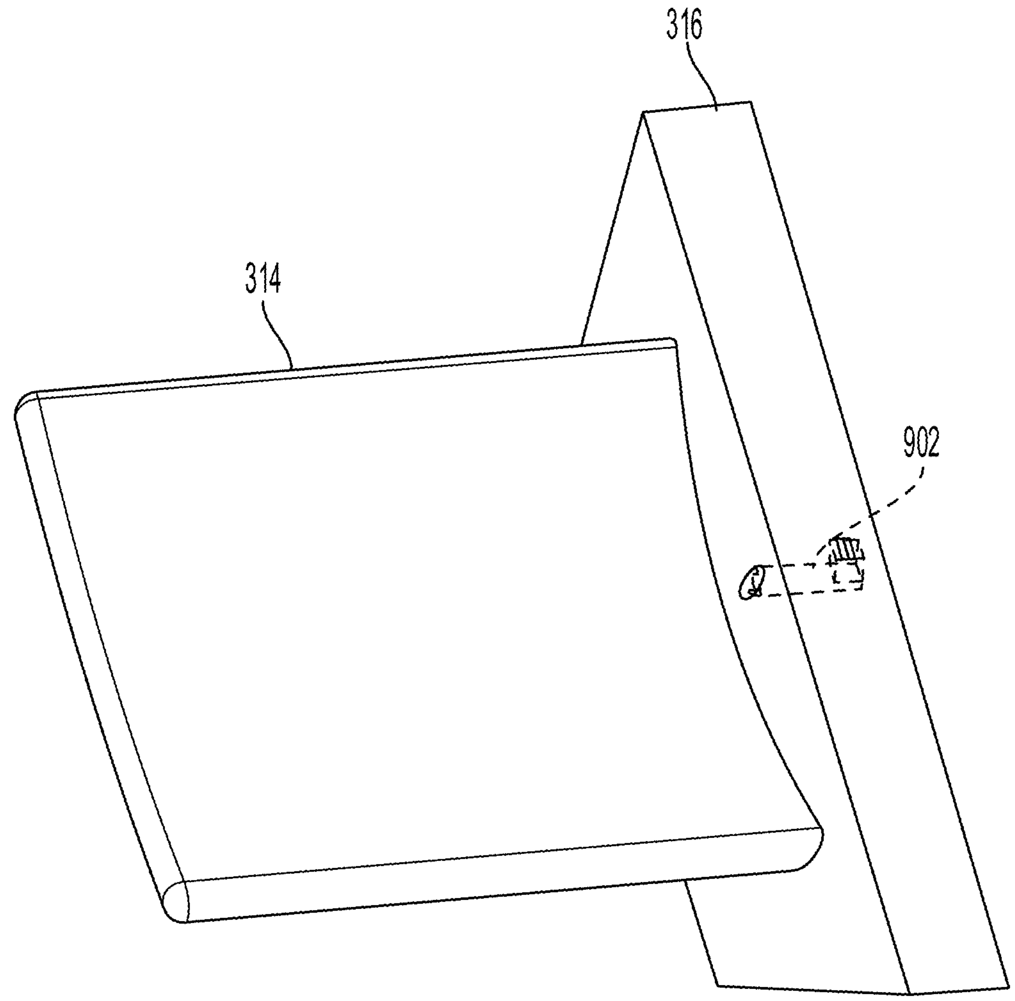
FIGS. 9A and 9B depict an example mechanical indicator that may be included in a phantom for visually indicating secure coupling of the phantom to a patient table.
Figure 9B:
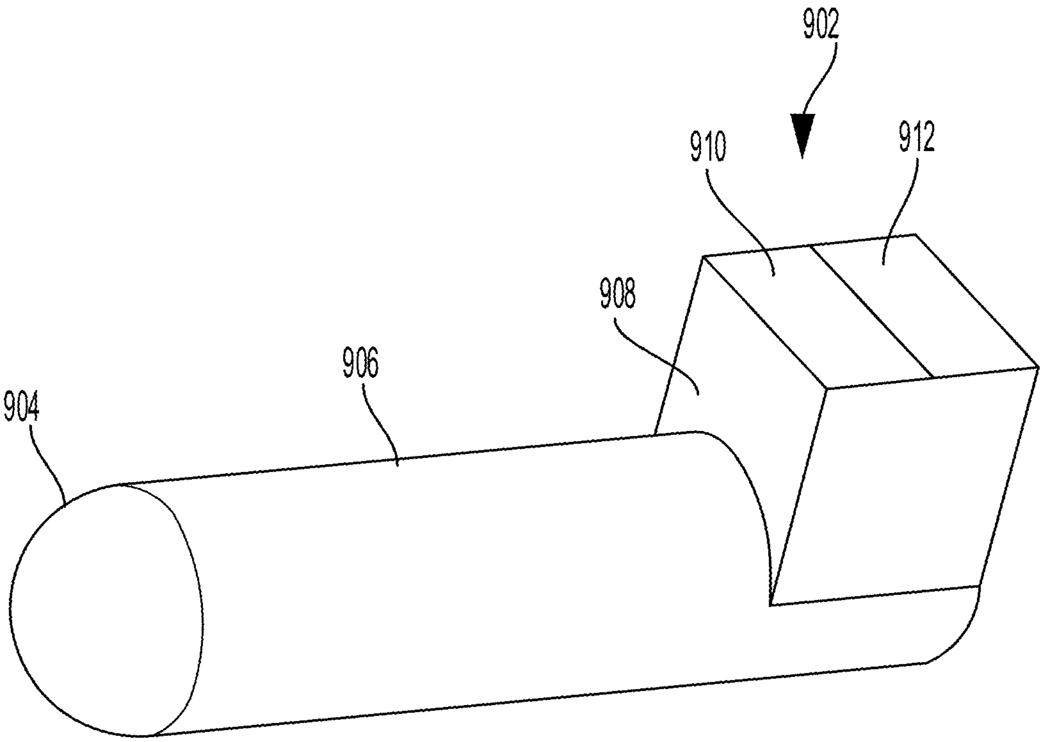

FIG. 9A depicts a mechanical indicator 902 that may be integrated into a plug base (e.g., plug base 316) of a phantom such as phantom 300. FIG. 9B is a magnified isolated view of the mechanical indicator 902. Specifically, FIG. 9A shows a cross-sectional view of a simplified version of the phantom 300 showing the plug 314 and a cross-section of the plug base 316. The mechanical indicator 902 may be located above the plug 314 within the plug base 316 and may be positioned so a contacting end 904 of the mechanical indicator 902 is positioned outside the plug base 316 and configured to make contact with a patient table above the accessory slot of the patient table when the plug 314 is installed in the accessory slot. The contacting end 904 may be hemispherical in shape and coupled to a cylindrical body 906 of the mechanical indicator 902. The cylindrical body 906 may be hollow and house a spring surrounding a bolt. The mechanical indicator 902 may further include a vertical indicator body 908 that houses a vertical extension of the bolt within the cylindrical body 906. The vertical indicator body 908 may include a top surface comprising a first indicator 910 and a second indicator 912. The first indicator 910 and the second indicator 912 may be visible from the exterior of the plug base 316 (e.g., the plug base 316 may include an opening on its top surface and the first indicator 910 or second indicator 912 may be visible via the opening). The second indicator 912 may be visible via the opening on the surface of the plug base 316 when the plug 314 of the phantom is not secured at a desired position within the accessory slot. However, when mechanical pressure is applied to the mechanical indicator 902, such as when the plug 314 is secured to the accessory slot and the contacting end 904 is brought in contact with the patient table, the vertical indicator body 908 may move relative to the plug base 316 so that the first indicator 910 may be visible via the opening on the surface of the plug base 316. In one example, the first indicator 910 may be a different color than the second indicator 912 (e.g., the first indicator 910 may be green and the second indicator 912 may be red, though other ways of visually distinguishing the first indicator 910 and the second indicator 912 are possible). When the first indicator 910 is visible, the user may know that the plug of the phantom has been inserted far enough in the accessory slot for a secure connection. When the phantom is removed from the patient table, the spring surrounding the bolt inside the cylindrical body 906 may urge the mechanical indicator 902 back to its original position where the second indicator 912 is visible. It is to be appreciated that while the mechanical indicator 902 is shown and described as being positioned on the phantom 300, the mechanical indicator 902 may additionally or alternatively be positioned on the phantom 700 and/or the phantom 800.

FIG. 10 is a side view of a phantom 700 placed within a PCCT system such as PCCT 100 and FIG. 11 is a perspective view of a phantom 700 within a PCCT system such as system 100. FIGS. 10 and 11 are described collectively. The phantom 700 is coupled to the table 114 by the plug 710 installed within the accessory slot of the table 114. The phantom 700 may be located within the gantry 102 by moving the table 114 horizontally (e.g., along the y axis) so that the phantom 700 is positioned at a desired horizontal position within the gantry 102 (e.g., dependent on which stack is to be scanned). Further, the table 114 may be moved vertically (e.g., along the z axis) to bring the phantom 700 to a desired vertical position, such as proximate the X-ray source 104. The x-ray source 104 produces an X-ray radiation beams 106 that impacts the phantom 700 and is attenuated by the phantom 700 before striking the detector 108. The phantom 700 is positioned in the X-ray radiation beam 106 with the X-ray beam 106 intersecting/passing through the first step 709. The width of the X-ray radiation beam 106 is equal to the width of the first step 709. Therefore, the X-ray radiation beam 106 is attenuated by a stack of material comprised of the first step 709, the second layer 706, the first layer 704, and the base 702. The horizontal position of the phantom 700 may be adjusted by moving adjusting the position of the table 114 in order to scan a different stack.

As appreciated in FIG. 11, the trapezoidal shape of the phantom 700 matches the shape of the X-ray radiation beam 106. Further, the X-ray source 104 is positioned on the gantry 102, on an opposite side of the gantry 102 as the bore in which the phantom 700 is placed. The trapezoidal shape of the phantom 700 allows the phantom 700 to be positioned close to the bottom of the gantry 102 due to the slanted sides of the phantom 700. Further, as appreciated in FIG. 10, the plug 710 may extend out from a vertical center of the phantom 700 (e.g., the center of the thickest part of the phantom 700, which may be the stack that includes the second step 711) and thus approximately half of the phantom 700 may extend below the plug 710, with at least some of the phantom extending below the table 114. This configuration allows the phantom 700 to be positioned closer to the bottom of the bore (and thus the X-ray source 104) than configurations where the phantom is positioned on the table 114, for example, while still holding the phantom 700 in a secure position during scanning. During a calibration scan, the gantry 102 may be positioned so that the X-ray source 104 is at a vertically lowest position and thus positioning the phantom 700 as shown allows the phantom 700 to be as close to the X-ray source 104 as possible during the calibration scan, which allows sufficient quality projection data to be obtained with relatively thin layers of material of the phantom. If the phantom were positioned farther from the X-ray source 104 during scanning, the layers of the phantom 700 may need to be thicker to obtain high quality projection data. Additionally, as shown in FIG. 10, the plug base 712 may have a slanted side that matches the angle of the front of the table 114. In some examples, the plug 710 of the phantom 700 may be inserted in the accessory slot farther than shown in FIG. 10 such that the slanted side of the plug base makes contact with the front of the table 114. In some examples, the front of the table 114 may include foam inserts to ensure a snug fit between the plug base 712 and the front of the table 114.

FIGS. 10 and 11 show the phantom 700 positioned in system 100, but it is to be appreciated that the phantom 300 and/or the phantom 800 may be positioned in system 100 in a similar manner. For example, the phantom 300 may be positioned at the front of the table 114 by inserting the plug 314 into the accessory slot until the plug base 316 of the phantom 300 contacts the front of the table 114. The table 114 may be moved vertically and horizontally to position a desired stack of the phantom 300 in the path of the X-ray radiation beam 106. The phantom 300 may extend with the base 302 above the X-ray source 104 and a portion of the base 302 below the table 114.

Figure 12:
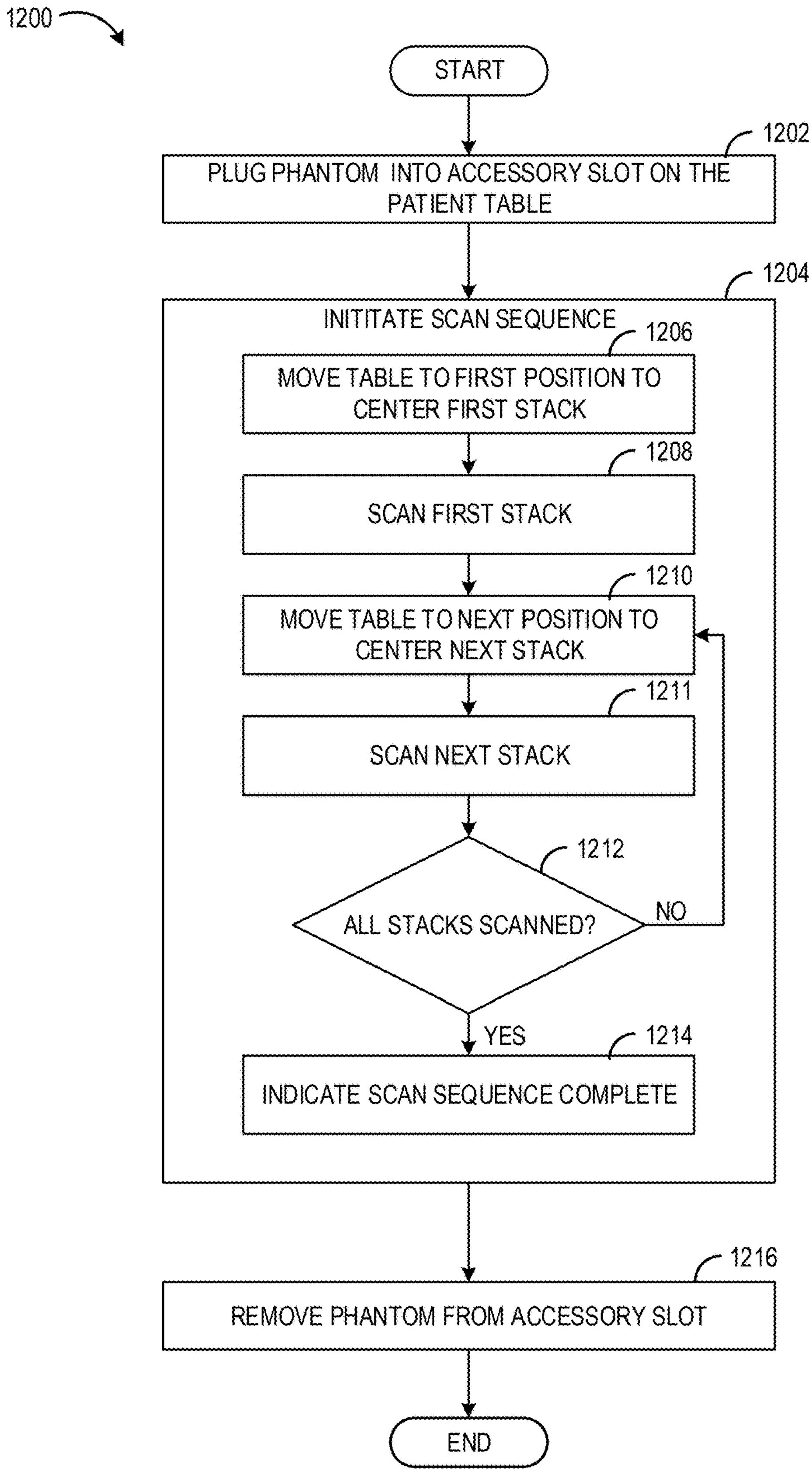
FIG. 12 is a flow chart illustrating a method for performing a calibration scan with a phantom according to embodiments of the present disclosure.

FIG. 12 is a method 1200 for using a phantom such as phantom 300 to calibrate a CT scanner such as the PCCT system shown in FIG. 1. At least some aspects of method 1200 may be carried out according to instructions stored in memory and executed by one or more processors of the PCCT system, such as via computing device 216. At 1202, method 1200 may include plugging the phantom into an accessory slot on a patient table. The phantom includes a plug that is configured to mate with the accessory slot on the patient table. When the plug is inserted completely into the accessory slot, the weight of the phantom may be supported by the plug secured in the accessory slot and the phantom may be securely fastened to the patient table. The phantom may include handles (integrated into the phantom or in a cover that is configured to be removably positioned on/around the phantom) so the phantom may be manipulated by one or more users in order to insert the plug into the accessory slot. At 1204, the method may include initiating a scan sequence for calibrating the PCCT system. The scan sequence may be initiated by the computing device in response to user input. At 1206, performing the scan sequence may include moving the table into a first position to center a first stack of the phantom at a scanning position (e.g., where the first stack will be in the path of an X-ray beam generated by an X-ray source of the PCCT system). In the example that the phantom 300 is being scanned, the first stack may include the base and the first layer. The table may be positioned so that the first stack is centered in the X-ray beam and may intercept the entire X-ray beam. At 1208, performing the scan sequence may include scanning the first stack. Scanning the first stack may include the PCCT system generating an X-ray beam that is attenuated by the first stack and detecting the photons of the attenuated X-ray beam at a detector of the PCCT system. At 1210, performing the scan sequence may include moving the table position to center the next stack at the scanning position. The next stack may be adjacent to the first stack on the phantom. For example, the second stack of the phantom 300 may include the base, the first layer, and the second layer. The table may be moved laterally to center the next stack at the scanning position. The trapezoidal shape of the phantom may allow for stacks that include more layers to match the width of the x-ray beam at the position of the surface of the stack without moving the patient table up or down. However, the table may still be moved up or down to adjust the position of the phantom, particularly prior to scanning the stacks. At 1211, the scan sequence may include scanning the next stack in the same manner that the first stack was scanned at 1206. At 1212, the scan sequence may include determining if all stacks have been scanned. If all stacks have not been scanned, the scan sequence may proceed to 1210 to center the next stack (e.g., a third stack, which may include the base, the first layer, the second layer, and a first step of a third layer; or a fourth stack, which may include the base, the first layer, the second layer, and a second step of the third layer). The moving of the table and scanning of the stacks may repeat until all stacks have been scanned. If all stacks have been scanned at 1212, the scan sequence may include indicating the scan sequence has been completed at 1214. If the scan sequence is completed, the method 1200 may include removing the phantom from the accessory slot at 1216.

Thus, the base and the plurality of layers of the phantom form a plurality of vertical stacks each configured to intersect an X-ray beam during a calibration scan. The plurality of vertical stacks may include a first vertical stack that includes the base and the first layer (and not the second layer or the third layer). During the calibration scan, the first vertical stack may be scanned with the table in a first position, such that the X-ray beam intersects the first vertical stack (and not any other vertical stacks of the phantom). The plurality of vertical stacks further includes a second vertical stack that includes the base, the first layer, and the second layer (and not the third layer). During the calibration scan, the second vertical stack may be scanned with the table in a second position, such that the X-ray beam intersects the second vertical stack (and not any other vertical stacks of the phantom). The plurality of stacks further includes a third vertical stack that includes the base, the first layer, the second layer, and a first step (e.g., thickness) of the third layer. During the calibration scan, the third vertical stack may be scanned with the table in a third position, such that the X-ray beam intersects the third vertical stack (and not any other vertical stacks of the phantom). The plurality of vertical stacks may include a fourth vertical stack that includes the base, the first layer, the second layer, and a second step (e.g., thickness) of the third layer. During the calibration scan, the fourth vertical stack may be scanned with the table in a fourth position, such that the X-ray beam intersects the fourth vertical stack (and not any other vertical stacks of the phantom).

It is to be appreciated that the scan sequence may include scanning the stacks in a reverse order (e.g., starting with the fourth stack and ending with the first stack). Further, depending on the calibration desired, not all stacks may be scanned. For example, some calibrations may dictate that only one stack (e.g., the third stack) be scanned, while other calibrations may dictate that only two or three stacks be scanned. By utilizing the single-piece phantom disclosed herein (e.g., phantom 300, phantom 700, or phantom 800), one or more desired stacks may be scanned without having to adjust any aspects of the phantom between scanning of the stacks other than moving the table to a desired scanning position.

The disclosure also provides support for a phantom for calibrating an imaging system, comprising: a base comprised of a first material, a plurality of layers positioned on the base, each layer of the plurality of layers comprised of the first material or one or more additional materials, and a plug coupled to a front face of the base and the plurality of layers, the plug configured to couple to an accessory slot of a patient table of the imaging system. In a first example of the system, the plurality of layers includes a first layer positioned on the base, a second layer positioned on the first layer, and a third layer positioned on the second layer. In a second example of the system, optionally including the first example, the base has a first length from the front face of the base to a back of the base, wherein the first layer has the first length, wherein the second layer has a second length, equal to or shorter than the first length, and wherein the third layer has a third length, equal to or shorter than the second length. In a third example of the system, optionally including one or both of the first and second examples, the base has a first height from a bottom of the base to a top of the base, wherein the first layer has a second height, smaller than the first height, and wherein the second layer has a third height, larger than the second height. In a fourth example of the system, optionally including one or more or each of the first through third examples, the third layer comprises a first step and a second step, wherein the first step has the third height, and wherein the second step has a fourth height, larger than the third height. In a fifth example of the system, optionally including one or more or each of the first through fourth examples, the phantom has slanted sides to form a trapezoid shape, such that a first width of the base is narrower than a second width of first layer, a third width of the second layer is wider than the second width, and a fourth width of the third layer is wider than the third width. In a sixth example of the system, optionally including one or more or each of the first through fifth examples, the base and the plurality of layers form a plurality of vertical stacks each configured to intersect an X-ray beam during a calibration scan. In a seventh example of the system, optionally including one or more or each of the first through sixth examples, the plurality of vertical stacks includes a first vertical stack that includes the base and the first layer, a second vertical stack that includes the base, the first layer, and the second layer, a third vertical stack that includes the base, the first layer, the second layer, and a first step of the third layer, and a fourth vertical stack that includes the base, the first layer, the second layer, and a second step of the third layer. In an eighth example of the system, optionally including one or more or each of the first through seventh examples, the system further comprises: a first handle extending on a first side of the base and a second handle extending on a second side of the base. In a ninth example of the system, optionally including one or more or each of the first through eighth examples, the system further comprises: a first arm and a second arm each extending out from the front face of the base and the plurality of layers, a fastening plate coupled to the first arm and the second arm, and a plug base coupled to the fastening plate, wherein the plug extends out from the plug base. In a tenth example of the system, optionally including one or more or each of the first through ninth examples, the system further comprises: a first handle extending on back of the base and a second handle extending from the first arm and the second arm. In an eleventh example of the system, optionally including one or more or each of the first through tenth examples, the system further comprises: a mechanical indicator configured to visually indicate a position of the phantom relative to the patient table.

The disclosure also provides support for a phantom system for an imaging system, comprising: a phantom comprising: a main body including a base comprised of a first material and a plurality of layers positioned on the base, each layer of the plurality of layers comprised of the first material or one or more additional materials, a plug, and a plug base coupled between the plug and the main body, the plug configured to couple to an accessory slot of a table of the imaging system, and a cover configured to accommodate the phantom. In a first example of the system, the cover includes integrated handles. In a second example of the system, optionally including the first example, the cover includes a top, a bottom, two sides, and a hollow interior accessible via a front opening. In a third example of the system, optionally including one or both of the first and second examples, the hollow interior is defined by inner surfaces of the top, the bottom, and the two sides, and has a size and a shape that is complementary to a size and shape of the main body of the phantom. In a fourth example of the system, optionally including one or more or each of the first through third examples, when the phantom is accommodated within the cover, the base and the plurality of layers are positioned in the hollow interior and the plug is positioned outside of the cover.

The disclosure also provides support for a method for calibrating an imaging system, comprising: positioning a phantom in a bore of the imaging system by moving a table of the imaging system, the phantom coupled to the table via a plug of the phantom accommodated within an accessory slot of the table, the phantom including a main body coupled to the plug, the main body including a base comprised of a first material and a plurality of layers positioned on the base, each layer of the plurality of layers comprised of the first material or one or more additional materials, and scanning a first vertical stack of the main body, the first vertical stack including at least the base and a first layer of the plurality of layers. In a first example of the method, the first vertical stack includes only the base and the first layer, and further comprising scanning a second vertical stack of the main body, the second vertical stack including the base, the first layer, and a second layer of the plurality of layers, and wherein the table is moved between the scanning of the first vertical stack and the scanning of the second vertical stack. In a second example of the method, optionally including the first example, positioning the phantom in the bore of the imaging system by moving the table comprises moving the table horizontally to position the phantom at a first scanning position for scanning the first vertical stack and moving the table vertically to position the phantom at a defined position relative to an X-ray source of the imaging system.

FIGS. 3-11 and 13 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A phantom for calibrating an imaging system, comprising:
- a base comprised of a first material;
- a plurality of layers positioned on the base, each layer of the plurality of layers comprised of the first material or one or more additional materials; and
- a plug coupled to a front face of the base and the plurality of layers, the plug configured to be inserted into an accessory slot of a patient table of the imaging system to position the phantom at the front of the patient table.

2. The phantom of the claim 1, wherein the plurality of layers includes a first layer positioned on the base, a second layer positioned on the first layer, and a third layer positioned on the second layer.

3. The phantom of claim 2, wherein the base has a first length from the front face of the base to a back of the base, wherein the first layer has the first length, wherein the second layer has a second length, equal to or shorter than the first length, and wherein the third layer has a third length, equal to or shorter than the second length.

4. The phantom of claim 2, wherein the base has a first height from a bottom of the base to a top of the base, wherein the first layer has a second height, smaller than the first height, and wherein the second layer has a third height, larger than the second height.

5. The phantom of claim 4, wherein the third layer comprises a first step and a second step, wherein the first step has the third height, and wherein the second step has a fourth height, larger than the third height.

6. The phantom of claim 2, wherein the phantom has slanted sides to form a trapezoid shape, such that a first width of the base is narrower than a second width of first layer, a third width of the second layer is wider than the second width, and a fourth width of the third layer is wider than the third width.

7. The phantom of claim 2, wherein the base and the plurality of layers form a plurality of vertical stacks each configured to intersect an X-ray beam during a calibration scan.

8. The phantom of claim 7, wherein the plurality of vertical stacks includes a first vertical stack that includes the base and the first layer; a second vertical stack that includes the base, the first layer, and the second layer; a third vertical stack that includes the base, the first layer, the second layer, and a first step of the third layer; and a fourth vertical stack that includes the base, the first layer, the second layer, and a second step of the third layer.

9. The phantom of claim 1, further comprising a first handle extending on a first side of the base and a second handle extending on a second side of the base.

10. The phantom of claim 1, further comprising a first arm and a second arm each extending out from the front face of the base and the plurality of layers, a fastening plate coupled to the first arm and the second arm, and a plug base coupled to the fastening plate, wherein the plug extends out from the plug base.

11. The phantom of claim 10, further comprising a first handle extending on back of the base and a second handle extending from the first arm and the second arm.

12. The phantom of claim 1, further comprising a mechanical indicator configured to visually indicate a position of the phantom relative to the patient table.

13. A phantom system for an imaging system, comprising:
- a phantom comprising:
  - a main body including a base comprised of a first material and a plurality of layers positioned on the base, each layer of the plurality of layers comprised of the first material or one or more additional materials;
  - a plug; and
  - a plug base coupled between the plug and the main body, the plug configured to be inserted into an accessory slot of a table of the imaging system to position the phantom at the front of the table; and
- a cover configured to accommodate the phantom.

14. The phantom system of claim 13, wherein the cover includes integrated handles.

15. The phantom system of claim 13, wherein the cover includes a top, a bottom, two sides, and a hollow interior accessible via a front opening.

16. The phantom system of claim 15, wherein the hollow interior is defined by inner surfaces of the top, the bottom, and the two sides, and has a size and a shape that is complementary to a size and shape of the main body of the phantom.

17. The phantom system of claim 16, wherein when the phantom is accommodated within the cover, the base and the plurality of layers are positioned in the hollow interior and the plug is positioned outside of the cover.

18. A method for calibrating an imaging system, comprising:
- positioning a phantom in a bore of the imaging system by moving a table of the imaging system, the phantom positioned at the front of the table via a plug of the phantom inserted into an accessory slot of the table, the phantom including a main body coupled to the plug, the main body including a base comprised of a first material and a plurality of layers positioned on the base, each layer of the plurality of layers comprised of the first material or one or more additional materials; and scanning a first vertical stack of the main body, the first vertical stack including at least the base and a first layer of the plurality of layers.

19. The method of claim 18, wherein the first vertical stack includes only the base and the first layer, and further comprising scanning a second vertical stack of the main body, the second vertical stack including the base, the first layer, and a second layer of the plurality of layers, and wherein the table is moved between the scanning of the first vertical stack and the scanning of the second vertical stack.

20. The method of claim 18, wherein positioning the phantom in the bore of the imaging system by moving the table comprises moving the table horizontally to position the phantom at a first scanning position for scanning the first vertical stack and moving the table vertically to position the phantom at a defined position relative to an X-ray source of the imaging system.

* * * * *